United States Patent
Takamori

(10) Patent No.: US 9,936,895 B2
(45) Date of Patent: Apr. 10, 2018

(54) MAGNETIC RESONANCE IMAGING APPARATUS, BED FOR MAGNETIC RESONANCE IMAGING APPARATUS AND A METHOD OF POSITIONING A BED FOR A MAGNETIC RESONANCE IMAGING APPARATUS

(71) Applicant: TOSHIBA MEDICAL SYSTEMS CORPORATION, Otawara-shi, Tochigi (JP)

(72) Inventor: Hiromitsu Takamori, Otawara (JP)

(73) Assignee: TOSHIBA MEDICAL SYSTEMS CORPORATION, Otawara-Shi, Tochigi-Ken ( * ) Notice: Subject to any disclaimer, the term of this patent is extended or adjusted under 35 U.S.C. 154(b) by 305 days.

(21) Appl. No.: 14/295,795

(22) Filed: Jun. 4, 2014

(65) Prior Publication Data
US 2014/0288410 A1  Sep. 25, 2014

Related U.S. Application Data

(63) Continuation of application No. PCT/JP2013/068187, filed on Jul. 2, 2013.

(30) Foreign Application Priority Data

Jul. 5, 2012 (JP) ................. 2012-151937

(51) Int. Cl.
*A61B 5/055* (2006.01)

(52) U.S. Cl.
CPC ................. *A61B 5/0555* (2013.01)

(58) Field of Classification Search
CPC ...................................... A61B 5/055
USPC ............................ 5/601, 613–619
See application file for complete search history.

(56) References Cited

U.S. PATENT DOCUMENTS

| | | | |
|---|---|---|---|
| 4,131,802 A * | 12/1978 | Braden | A61B 6/0442 250/363.02 |
| 4,671,728 A | 6/1987 | Clark et al. | |
| 6,776,527 B1 * | 8/2004 | Tybinkowski | A61B 6/04 378/195 |
| 7,696,752 B2 | 4/2010 | Takamori | |
| 8,984,684 B2 | 3/2015 | Ninomiya et al. | |

(Continued)

FOREIGN PATENT DOCUMENTS

| | | |
|---|---|---|
| JP | 1985-015304 | 2/1985 |
| JP | 62-14842 | 1/1987 |

(Continued)

OTHER PUBLICATIONS

International Search Report for PCT/JP2013/068187 dated Aug. 6, 2013.

(Continued)

*Primary Examiner* — Fredrick C Conley
(74) *Attorney, Agent, or Firm* — Nixon & Vanderhye P.C.

(57) ABSTRACT

According to one embodiment, a magnetic resonance imaging apparatus includes a gantry and a movable bed. A magnet, a gradient coil, and a radio frequency coil are built in the gantry. The movable bed is configured to be positioned to the gantry by a positioning mechanism having different structures at different positions in a longitudinal direction of the bed.

15 Claims, 9 Drawing Sheets

(56) References Cited

U.S. PATENT DOCUMENTS

| | | | |
|---|---|---|---|
| 2005/0269514 A1* | 12/2005 | Stark | A61B 6/04 250/363.08 |
| 2006/0167356 A1* | 7/2006 | Everett | A61B 6/0457 600/407 |
| 2013/0096419 A1* | 4/2013 | Miyazaki | G01R 33/56308 600/419 |

FOREIGN PATENT DOCUMENTS

| | | |
|---|---|---|
| JP | 2008-036400 | 2/2008 |
| WO | WO 2012/043019 A1 | 4/2012 |

OTHER PUBLICATIONS

Notification of Transmittal of Translation of the International Preliminary Report on Patentability in PCT/JP2013/068187 dated Jan. 15, 2015.

Office Action dated Apr. 28, 2015 in CN Patent Application No. 201380001253.4.

* cited by examiner

MAGNETIC RESONANCE IMAGING APPARATUS, BED FOR MAGNETIC RESONANCE IMAGING APPARATUS AND A METHOD OF POSITIONING A BED FOR A MAGNETIC RESONANCE IMAGING APPARATUS

CROSS REFERENCES TO RELATED APPLICATIONS

This is a continuation of Application PCT/JP2013/68187, filed on Jul. 2, 2013.

This application is based upon and claims the benefit of priority from Japanese Patent Application No. 2012-151937, filed Jul. 5, 2012; the entire contents of which are incorporated herein by reference.

FIELD

Embodiments described herein relate generally to an MRI (magnetic resonance imaging) apparatus, a bed for a magnetic resonance imaging apparatus and a method of positioning a bed for a magnetic resonance imaging apparatus.

BACKGROUND

Conventionally, a movable bed used for an MRI apparatus is used with docking with one side of the gantry.

PRIOR TECHNICAL LITERATURE

[Patent literature 1] JPA 2008-36400

A movable bed used in an MRI apparatus is desired to be positioned easily with a simple structure.

Accordingly, an object of the present invention is to provide a magnetic resonance imaging apparatus, a bed for a magnetic resonance imaging apparatus and a method of positioning a bed for a magnetic resonance imaging apparatus which can position a movable bed easily.

DETAILED DESCRIPTION

In general, according to one embodiment, a magnetic resonance imaging apparatus includes a gantry and a movable bed. A magnet, a gradient coil, and a radio frequency coil are built in the gantry. The movable bed is configured to be positioned to the gantry by a positioning mechanism having different structures at different positions in a longitudinal direction of the bed.

Further, according to another embodiment, a bed for a magnetic resonance imaging apparatus includes a bed main body, a first positioning mechanism and a second positioning mechanism. The bed main body includes a top plate configured to set an object. The first positioning mechanism is configured to perform a positioning of the bed main body at a first position. The second positioning mechanism is configured to perform a positioning of the bed main body at a second position different from the first position in a longitudinal direction of the bed main body. The second positioning mechanism has a structure different from a structure of the first positioning mechanism.

Further, according to another embodiment, a method of positioning a movable bed for a magnetic resonance imaging apparatus includes positioning the bed, to a gantry of the magnetic resonance imaging apparatus, at a first position, by a first positioning mechanism; and positioning the bed, to the gantry, at a second position different from the first position in a longitudinal direction of the bed, by a second positioning mechanism having a structure different from a structure of the first positioning mechanism.

A magnetic resonance imaging apparatus, a bed for a magnetic resonance imaging apparatus and a method of positioning a bed for a magnetic resonance imaging apparatus according to embodiments of the present invention will be described with reference to the accompanying drawings.

(First Embodiment)

Figure 1:
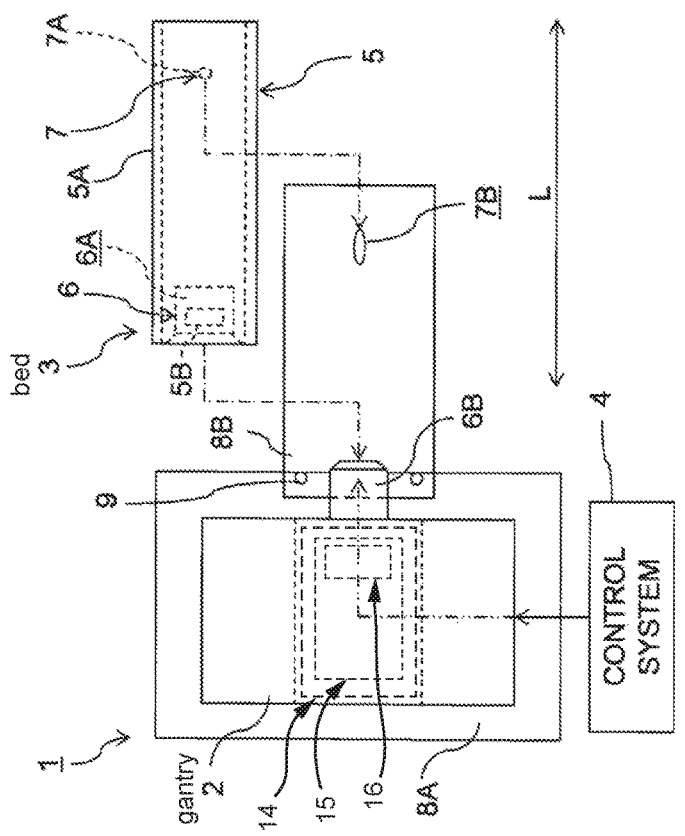
FIG. 1 is an upper view showing a configuration of a magnetic resonance imaging apparatus according to the first embodiment of the present invention.
Figure 2:
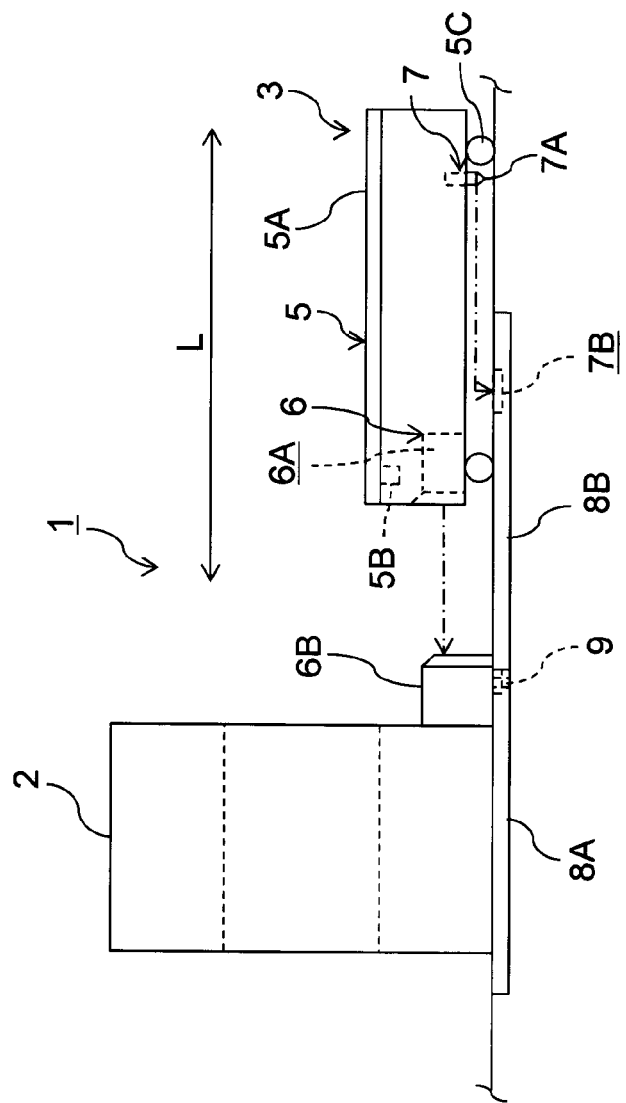
FIG. 2 is a front view of the gantry and the bed shown in FIG. 1.

FIG. 1 is an upper view showing a configuration of a magnetic resonance imaging apparatus according to the first embodiment of the present invention. Moreover, FIG. 2 is a front view of the gantry and the bed shown in FIG. 1.

A magnetic resonance imaging apparatus 1 includes a gantry 2, a bed 3, and a control system 4. Hardware, such as a magnet 14, a gradient coil 15, RF (radio frequency) coils 16, required for MR (magnetic resonance) imaging are built in the gantry 2. The control system controls the hardware built in the gantry 2 and the bed 3, and reconstructs MR image data based on MR signals received by RF reception coils.

The bed 3 is a movable bed which can be detached from and attached to the gantry 2, FIG. 1 shows an upper view of the bed 3 and the gantry 2 in the state where the bed 3 is not connected with the gantry 2. The bed 3 is configured to be fixable and detachable at mutually different positions in the longitudinal direction L. Then, the bed 3 can be positioned to the gantry 2 by fixing the bed 3 on the plural positions. Especially the bed 3 is configured to be positioned to the gantry 2 by positioning mechanisms having mutually different structures at mutually different positions in the longitudinal direction, In the example shown in FIG. 1, the bed 3 is fixed at two positions in the longitudinal direction L. Therefore, the bed 3 is configured by providing the first positioning mechanism 6 and the second positioning mechanism 7 with a bed main body 5.

The typical bed main body 5 has a top plate 5A for setting an object, a driving mechanism 5B for driving the top plate 5A and casters 5C for moving the bed main body 5, as illustrated. The driving mechanism 5B is controlled by electric power supplied from the control system 4 through the gantry 2. Meanwhile, the bed main body 5 is configured to be restricted to move horizontally by locking the drive of the casters 5C.

The first positioning mechanism 6 and the second positioning mechanism 7 are elements for positioning the bed main body 5 at the first position and the second position, respectively. Note that, the second position differs from the first position in the longitudinal direction L of the bed main body 5.

Specifically, the first positioning mechanism 6 is for horizontal positioning of the bed main body 5 at the first position in the side near the gantry 2. On the other hand, the second positioning mechanism 7 is for horizontal positioning of the bed main body 5 at the second position in the side separated from the gantry 2.

Moreover, the first positioning mechanism 6 and the second positioning mechanism 7 are configured to perform positioning respectively in the state where the casters 5C have contacted with the floor. Therefore, the bed main body 5 is configured to be positioned in the height direction of the top plate 5A by contacting the casters 5C with the floor.

For the first positioning mechanism 6 and the second positioning mechanism 7, arbitrary elements can be used so long as they are detachable and can perform the relative positioning of the bed main body 5 against the gantry 2. For example, the positioning mechanism can be configured by a hole and a pin inserted in the hole. Alternatively, the positioning mechanism can be also configured by a slot and a protruding object, such as a hook or a pin, fitting the slot. However, as mentioned above, the second positioning mechanism 7 has a structure different from that of the first positioning mechanism 6.

In the example shown in FIG. 1, a rectangular concave part 6A is formed in the bed main body 5 as the first positioning mechanism 6 while a pin 7A is prepared in the bed main body 5 as the second positioning mechanism 7. On the other hand, a convex part 6B, which fits to the rectangular concave part 6A consisting of the first positioning mechanism 6, is prepared near the floor in the bed 3 side of the gantry 2 while a slotted hole 7B, which fits to the pin 7A consisting of the second positioning mechanism 7, is formed at a position, separated from the gantry 2, on the floor.

However, targets on which the concave part and the convex part are formed may be converse. For example, a convex part may be provided with the bed main body 5 as the first positioning mechanism 6 while a concave part may be formed on the gantry 2. Moreover, a slotted hole or a slot may be formed on the bed main body 5 as the second positioning mechanism 7 while a pin may be fixed on the floor surface. Furthermore, inserting a pin into a hole formed on the floor surface and forming a slot, fitting the pin, on the bed main body 5 make it possible to attach and detach the bed 3 easily.

The bed 3 is preferred to be fixed detachably to the gantry 2 at least one place. That is, the positioning accuracy of the bed 3 to the gantry 2 can be improved by connecting the bed 3 with the gantry 2 directly. On the other hand, the direction of the bed 3 to the gantry 2 can be set accurately by fixing the bed 3 detachably at another place farther from the gantry 2.

Moreover, the plate for fixing the bed 3 in the side separated from the gantry 2 may be an element of the magnetic resonance imaging apparatus 1. The plate for fixing the bed 3 so as to be detachable is desired to be rigidly connected with the gantry 2. In the example shown in FIG. 1, a floor plate 8A for installing the gantry 2 is rigidly connected with a floor plate 8B for installing the bed 3 by fixing members 9, such as bolts. Thus, it becomes possible to fix the bed 3 to the gantry 2 firmly with a higher accuracy by rigidly connecting the plate with the gantry 2.

When a plate is provided, the positioning mechanism of the bed 3 can be configured easily by forming a hole or a slot on at least one of the bed 3 and the plate and providing a pin or a hook, inserted in the hole or the slot, with the other. In the example shown in FIG. 1, a slotted hole 7B is formed on the plate while a pin 7A which fits the slotted hole 7B is provided with the bed 3.

As shown in FIG. 1, the bed 3 can be configured to be positioned, at a position in the side far from the gantry 2, with the slotted hole 7B and the pin 7A which is inserted in the slotted hole 7B. Thereby, the mechanical errors in the longitudinal direction L of the bed 3 can be reduced.

Note that, the second positioning mechanism 7 to position the bed 3 at a position in the side away from the gantry 2 may be also configured to operate in conjunction with the positioning of the bed 3 at a position of the bed 3 in the gantry 2 side by the first positioning mechanism 6.

Figure 3:
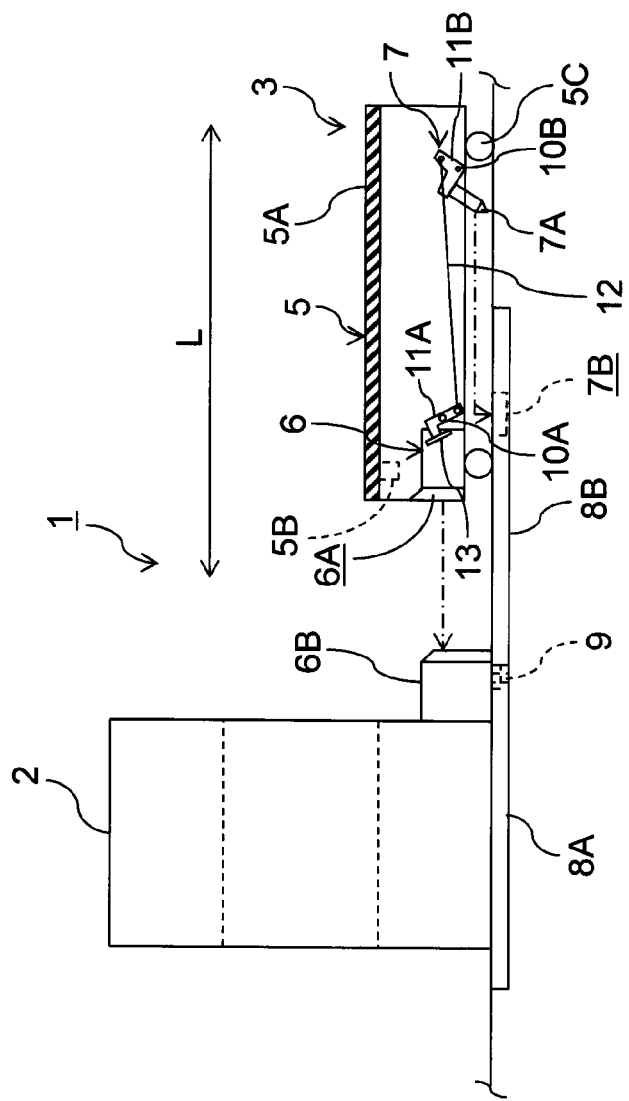
FIG. 3 is a view showing an example of configuration of the second positioning mechanism for fixing the bed shown in FIG. 1 in case where the second positioning mechanism is configured to move with interlocking with the fixation at the position in the gantry side.

FIG. 3 is a view showing an example of configuration of the second positioning mechanism 7 for fixing the bed 3 shown in FIG. 1 in case where the second positioning mechanism 7 is configured to move with interlocking with the fixation at the position in the gantry 2 side. Moreover, FIG. 4 is a view showing the state of the second positioning mechanism 7 when the bed 3 shown in FIG. 3 has been set to the gantry 2.

Figure 4:
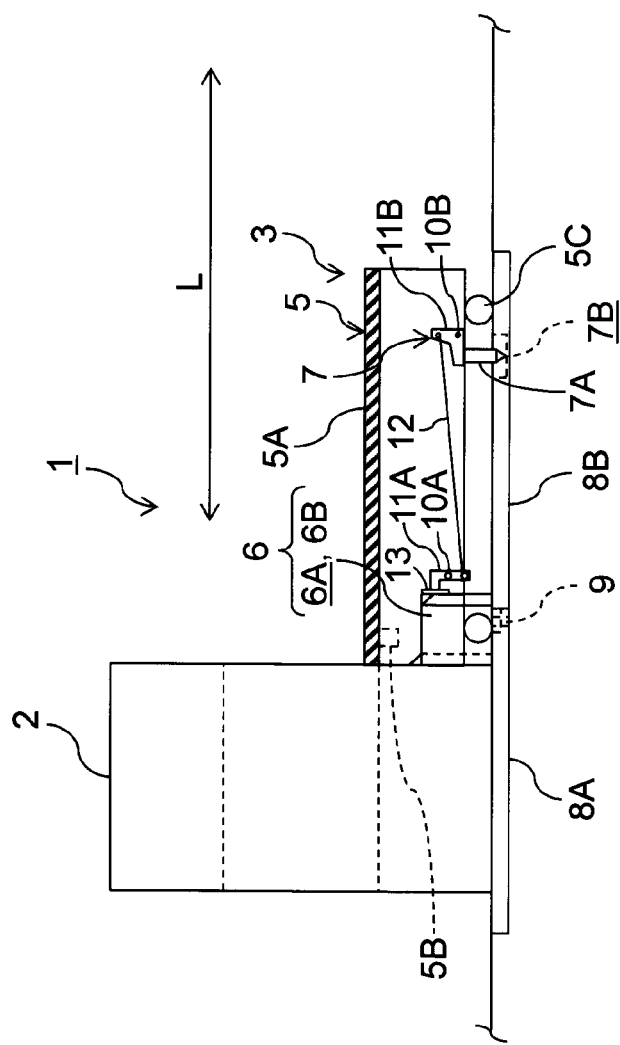
FIG. 4 is a view showing the state of the second positioning mechanism when the bed shown in FIG. 3 has been set to the gantry.

FIG. 3 shows the state where the bed 3 has been removed from the gantry 2 while FIG. 4 shows the state where the bed 3 has been set to the gantry 2. As shown in FIG. 3, rotary shafts 10A, 10B can be prepared in the gantry 2 side of the bed 3 and the side separated from the gantry 2, respectively. Further, L-shaped members 11A, 11B can be attached to the rotary shafts 10A, 10B, respectively. The ends of the L-shaped members 11A, 11B are connected with each other by connecting members 12, such as wires or connecting rods, whose both ends are free ends.

The L-shaped member 11A provided in the gantry 2 side is attached to the bed 3 so as to be an inverted L-shape. To the end of the L-shaped member 11A in the gantry 2 side, a contacting plate 13 is fixed. The contacting plate 13 contacts with the convex part 6B in the gantry 2 side when the bed 3 is set to the gantry 2. Moreover, the other end side of the L-shaped member 11A is rotatably connected with the connecting member 12.

On the other hand, the bed main body 5 side of the L-shaped member 11B provided in the side away from the gantry 2 is rotatably connected with the connecting member 12. Moreover, the pin 7A which fits the slotted hole 7B formed on the floor plate 8B is fixed to the other side of the L-shaped member 11B.

The L-shaped member 11A provided on the bed main body 5 in the gantry 2 side is laid counterclockwise with a spring. On the other hand, the L-shaped member 11B provided on the bed main body 5 in the side away from the gantry 2 is laid clockwise with a spring. For this reason, in the state that the contacting plate 13 of the L-shaped member 11A provided in the gantry 2 side does not contact with the convex part 6B in the gantry 2 side, the axis of the pin 7A becomes a diagonal direction by the action of the springs and the position of the pin 7A becomes high. Therefore, the bed 3 can be moved without the tip of the pin 7A contacting with the floor plate 8B.

On the other hand, when the contacting plate 13 is contacted with the convex part 6B in the gantry 2 side, the L-shaped member 11A provided in the gantry 2 side rotates clockwise. For this reason, the L-shaped member 11B provided in the side far from gantry 2 and connected with the connecting member 12 rotates counterclockwise. As a result, the pin 7A projects in the floor plate 8B side and the pin 7A can be inserted in the slotted hole 7B. That is, the bed 3 can be fixed at the two places.

In addition, chamfering members, such as the pin 7A, the slotted hole 7B, the convex part 6B and the concave part 6A, to be fitting targets as illustrated makes it possible to set and detach the bed 3 easily.

Figure 5:
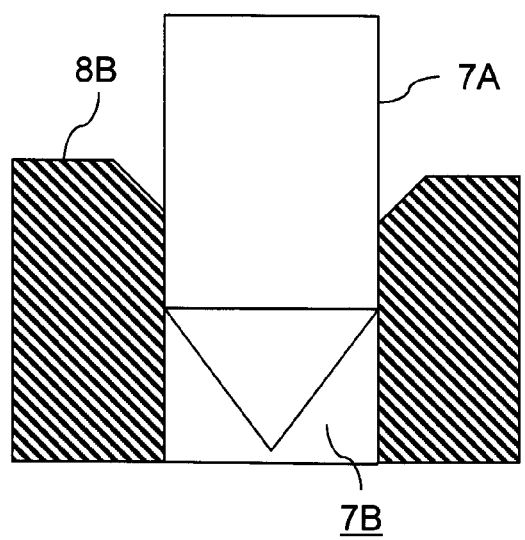
FIG. 5 is a view showing an example of forming a taper face on the slotted hole shown in FIG. 1.

FIG. 5 is a view showing an example of forming a taper face on the slotted hole 7B shown in FIG. 1.

FIG. 5 is a sectional view of the floor plate 8B as viewed from the longitudinal direction of the slotted hole 7B. As shown in FIG. 5, it becomes possible to guide the pin 7A into the slotted hole 7B easily by forming a tapered face on the slotted hole 7B. It is also suitable to form a tapered face on the tip of the pin 7A as illustrated.

The above mentioned magnetic resonance imaging apparatus 1 is an apparatus configured to position the movable bed 3 at two or more places in the longitudinal direction L by plural positioning mechanisms having mutually different structures.

For this reason, with the magnetic resonance imaging apparatus 1, the relative positional relationship between the bed 3 and the gantry 2 can be ensured with a higher accuracy. Especially, the conventional bed had been fixed to the gantry only in the gantry side. For this reason, in order to counter the component of the external force which is orthogonal to the longitudinal direction L of the bed, a very powerful docking mechanism was needed to be provided. Moreover, ensuring the positioning accuracy in the direction which is orthogonal to the longitudinal direction L of the bed was difficult.

On the contrary, with the magnetic resonance imaging apparatus 1, the bed 3 can be firmly fixed to the gantry 2 with a simple structure. Moreover, because the bed 3 is also fixed in the side, away from the gantry 2, of the bed 3, the positioning accuracy in the direction which is orthogonal to the longitudinal direction L of the bed 3 can be improved. In addition, the durability and the reliability of the docking mechanism which is used repeatedly can be improved because the docking mechanism of the bed 3 can be simplified.

Furthermore, with the magnetic resonance imaging apparatus 1, the movable bed 3 can be positioned easily. That is, at different positions in the longitudinal direction L of the bed 3, the positioning mechanisms, which have structures each depending on a positioning accuracy required corresponding to a distance from the gantry 2, are provided.

Specifically, at the first position in the side close to the gantry 2, high-precision positioning in the longitudinal direction L of the bed main body 5 and in the direction orthogonal to the longitudinal direction L is performed by the first positioning mechanism 6. On the other hand, at the second position in the side away from the gantry 2, only rough positioning in the direction orthogonal to the longitudinal direction L of the bed main body 5 is performed by the second positioning mechanism 7.

For this reason, a time-consuming positioning task to ensure an excessive positioning accuracy can be avoided. In other words, by changing a structure of positioning mechanism depending on a position in the longitudinal direction L of the bed 3, a positioning mechanism which can be set easily and satisfies at least a required positioning accuracy can be adopted.

(Second Embodiment)

Figure 6:
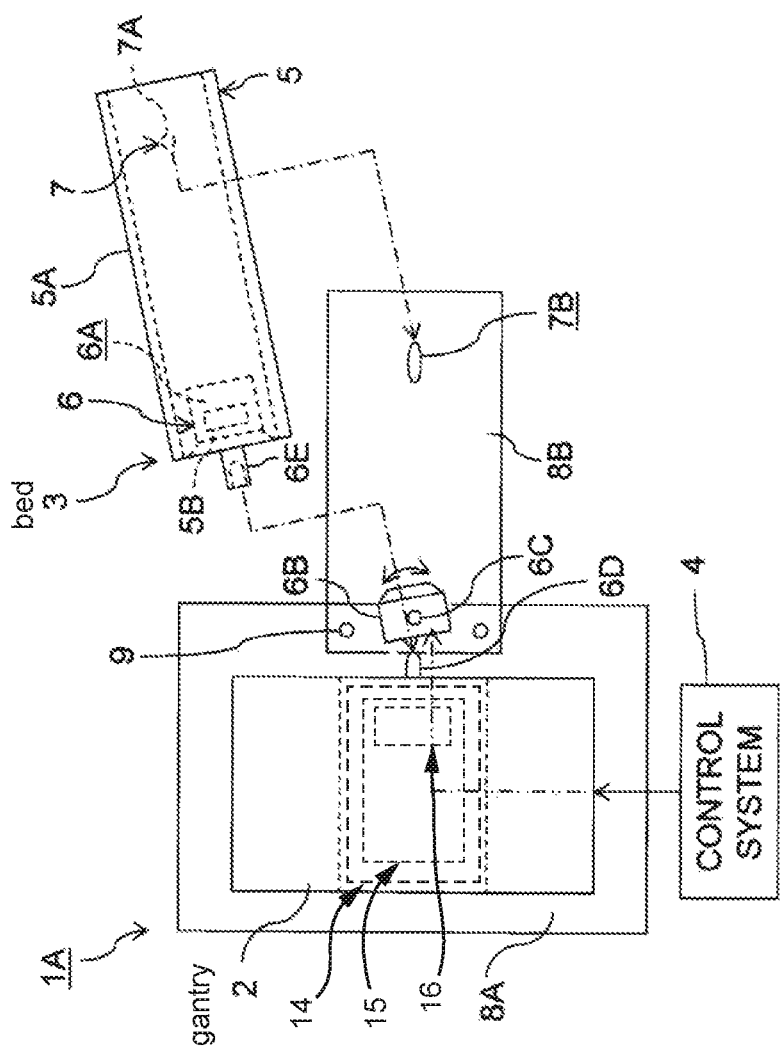
FIG. 6 is an upper view showing a configuration of a magnetic resonance imaging apparatus according to the second embodiment of the present invention.
Figure 7:
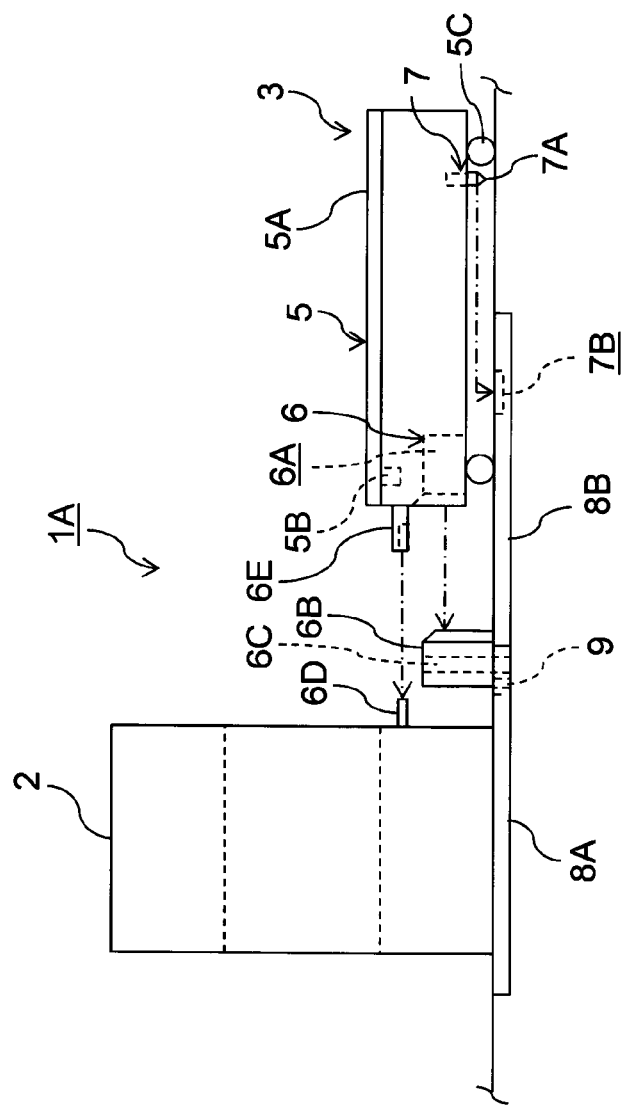
FIG. 7 is a front view of the gantry and the bed shown in FIG. 6.

FIG. 6 is an upper view showing a configuration of a magnetic resonance imaging apparatus according to the second embodiment of the present invention. Moreover, FIG. 7 is a front view of the gantry and the bed shown in FIG. 6. However, the direction of the bed shown in FIG. 7 is not coincident with that shown in FIG. 6.

In a magnetic resonance imaging apparatus 1A in the second embodiment, a structure of the first positioning mechanism 6 is different from that in the magnetic resonance imaging apparatus 1 in the first embodiment. Since the other configurations and actions of the magnetic resonance imaging apparatus 1A in the second embodiment do not differ from those of the magnetic resonance imaging apparatus 1 in the first embodiment substantially, same signs are attached to the same configurations and explanations thereof are omitted.

As shown in FIG. 6, the concave part 6A in the bed 3 side and the convex part 6B in the gantry 2 side can constitute the first positioning mechanism 6. In addition, the convex part 6B can be configured to rotate horizontally by providing a rotary shaft 6C with the convex part 6B. Therefore, even if the bed 3 is moved closer to the gantry 2 from an oblique direction, the concave part 6A in the bed 3 side can be fitted to the convex part 6B in the gantry 2 side.

Furthermore, a U-shaped convex part 6D is fixed to the gantry 2 side as an element of the first positioning mechanism 6. On the other hand, a convex part 6E, which has a concave fitting to the U-shaped convex part 6D, is fixed to the bed 3 side as an element of the first positioning mechanism 6.

Therefore, when the convex part 6D in the gantry 2 side is pushed into the convex part 6E in the bed 3 side by making the bed 3 approach the gantry 2, the longitudinal direction of the bed 3 gradually turns into the suitable direction corresponding to the direction of the gantry 2. As a result, the pin 7A in the bed 3 side which composes the second positioning mechanism 7 can be fitted into the slotted hole 713 on the floor plate 8B.

On the contrary, in the state that the tip of the U-shaped convex part 6D has been partially inserted in the convex part 6E having the U-shaped dent, the direction of the bed 3 can be adjusted. Therefore, after temporarily fixing the bed 3 by partially inserting the tip of the U-shaped convex part 6D in the convex part 6E having the U-shaped dent, the bed 3 can be locked by fitting the pin 7A, in the bed 3 side, into the slotted hole 7B of the floor plate 8B.

Thus, the bed 3 can be configured to be positioned in the horizontal direction at the first position in the side close to the gantry 2 and subsequently be positioned in the horizontal direction at the second position in the side far from the gantry 2. That is, the bed 3 can be configured to be temporarily fixed by the positioning in the horizontal direction at the first position in the side close to the gantry 2 and subsequently be locked by the positioning in the horizontal direction at the second position in the side away from the gantry 2.

Note that, the first positioning mechanism 6 may have another structure as long as the structure allows adjusting the direction of the bed 3, in the horizontal direction, against the gantry 2. For example, the U-shaped convex part 6D and the convex part 6E having the U-shaped dent may be omitted. Also in such a case, the temporary joint and the adjustment of direction of the bed 3 can be performed by rotating the convex part 6B in the gantry 2 side.

Moreover, as another example, the convex part 6B in the gantry 2 side may be unable to be rotated while the length of the U-shaped convex part 6D and the convex part 6E having the U-shaped dent may be made to be enough longer than the length of the convex part 6B. In that case, the temporary joint and the adjustment of direction of the bed 3 can be performed by the U-shaped convex part 6D and the convex part 6E having the U-shaped dent.

According to the magnetic resonance imaging apparatus 1A in the second embodiment as mentioned above, an effect similar to that in the magnetic resonance imaging apparatus 1 in the first embodiment can be obtained. In addition, even if the bed 3 is moved closer to the gantry 2 from an oblique direction, the bed 3 can be positioned. For this reason, it becomes possible to position the bed 3 still more easily.

(Third Embodiment)

Figure 8:
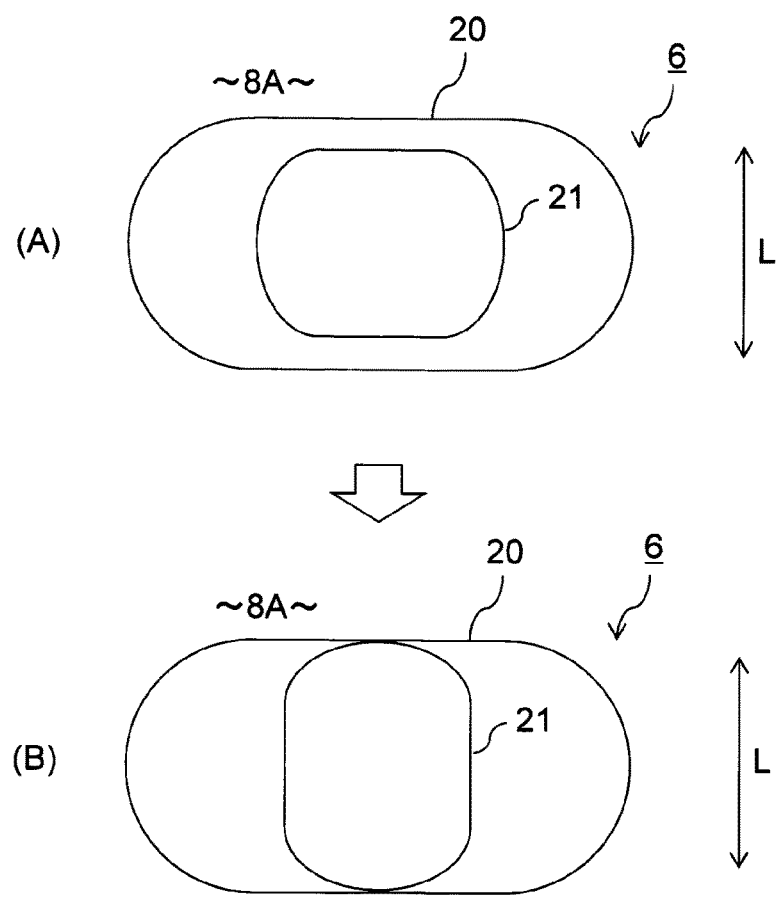
FIG. 8 is an upper view showing a configuration of the first positioning mechanism included in a magnetic resonance imaging apparatus according to the third embodiment of the present invention.

FIG. 8 is an upper view showing a configuration of the first positioning mechanism included in a magnetic resonance imaging apparatus according to the third embodiment of the present invention.

In a magnetic resonance imaging apparatus in the third embodiment, a structure of the first positioning mechanism 6 is different from that in the magnetic resonance imaging apparatus 1 in the first embodiment. The other configurations and actions of the magnetic resonance imaging apparatus in the third embodiment do not differ from those of the magnetic resonance imaging apparatus 1 in the first embodiment substantially. Therefore, only a structure of the first positioning mechanism 6 is illustrated with attaching same signs to the same configurations, and explanations of the same configurations are omitted.

The first positioning mechanism 6 included in the magnetic resonance imaging apparatus in the third embodiment has at least one slotted hole 20 and pin 21 whose cross section is a long circle. It is preferable to prepare two or more combinations consisting of the slotted holes 20 and the pins 21 in the direction normal to the longitudinal direction L of the bed 3 after the positioning.

When the slotted holes 20 are formed on the floor plate 8A, the pins 21 are attached to the bed 3 side. On the contrary, when the pins 21 are prepared on the floor plate 8A, the slotted holes 20 are formed in the bed 3 side. A method of attaching the pins 21 to the bed 3 or the floor plate 8A is arbitrary. However, the pins 21 are attached to the bed 3 or the floor plate 8A so that the pins 21 can rotate around their axes.

On the other hand, the longitudinal direction of each slotted hole 20 which constitutes the first positioning mechanism 6 is directed so as to be normal to the longitudinal direction of the slotted hole 7B of the floor plate 8B which constitutes the second positioning mechanism 7. That is, the longitudinal direction of each slotted hole 20 which constitutes the first positioning mechanism 6 is normal to the longitudinal direction L of the bed 3 after the positioning.

In the illustrated example, each slotted hole 20 is formed on the floor plate 8A. Therefore, the pins 21 are attached to the bed 3 side by an arbitrary method. For example, slotted holes are also formed on the bed 3 and the pins 21 are inserted into the slotted holes of the bed 3 so that the tips of the pins 21 project from the bed 3.

Note that, it is practical to prepare the convex part 6B in the gantry 2 side and to prepare the concave part 6A in the bed 3 side, respectively, as shown in FIG. 1, from a viewpoint of supplying electric power to the driving mechanism 5B of the top plate 5A and the like. Further, a sufficient interspace is formed between the convex part 6B in the gantry 2 side and the concave part 6A in the bed 3 side.

When the longitudinal direction of the pin 21 is turned to the longitudinal direction of the slotted hole 20 as shown in FIG. 8 (A), interspace is made between the pin 21 and the slotted hole 20. Therefore, the pin 21 can be slid, in the longitudinal direction of the slotted hole 20, in the slotted hole 20. On the other hand, when the longitudinal direction of the pin 21 is turned to the vertical direction to the longitudinal direction of the slotted hole 20 as shown in FIG. 8 (B), the pin 21 fits the slotted hole 20.

Therefore, when the pin 21 is inserted in the slotted hole 20 in the state where the longitudinal direction of the pin 21 has been turned to the longitudinal direction of the slotted hole 20, the bed 3 can be temporarily fixed in the gantry 2 side. Further, the position of the bed 3 can be finely adjusted in the longitudinal direction of the slotted hole 20. For this reason, the pin 7A in the bed 3 side which composes the second positioning mechanism 7 can be fitted with the slotted hole 7B of the floor plate 8B, with adjusting the position of the bed 3 in the direction orthogonal to the longitudinal direction L of the bed 3. After that, the bed 3 can be locked in the gantry 2 side by rotating the pin 21 which composes the first positioning mechanism 6.

That is, the first positioning mechanism 6 included in the magnetic resonance imaging apparatus in the third embodiment has a structure which can adjust the position of the bed 3 in the direction orthogonal to the longitudinal direction L.

Therefore, according to the magnetic resonance imaging apparatus in the third embodiment, an effect similar to that in the magnetic resonance imaging apparatus 1 in the first embodiment can be obtained. In addition, the bed 3 can be positioned horizontally at the second position in the side separated from the gantry 2 after horizontal positioning at the first position in the side near the gantry 2. Moreover, the bed 3 can be temporary installed by the horizontal positioning at the first position in the side near the gantry 2 and subsequently the bed 3 can be locked by the horizontal positioning at the second position in the side separated from the gantry 2.

Note that, the pin 21 which composes the first positioning mechanism 6 may be a normal pin whose cross section is circular. In that case, making a diameter of a circular pin into a size fitted with the slotted hole 20 allows a more accurate positioning in the longitudinal direction L of the bed 3 even if there is a gap between the convex part 6B in the gantry 2 side and the concave part 6A in the bed 3 side.

(Fourth Embodiment)

Figure 9:
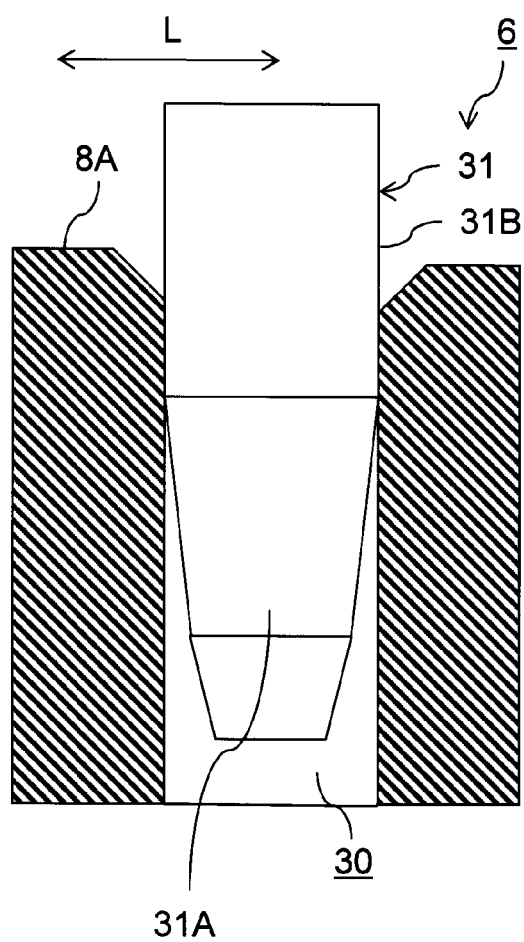
FIG. 9 is a longitudinal sectional view showing a configuration of the first positioning mechanism included in a magnetic resonance imaging apparatus according to the fourth embodiment of the present invention.

FIG. 9 is a longitudinal sectional view showing a configuration of the first positioning mechanism included in a magnetic resonance imaging apparatus according to the fourth embodiment of the present invention.

In a magnetic resonance imaging apparatus in the fourth embodiment, a structure of the first positioning mechanism 6 is different from that in the magnetic resonance imaging apparatus 1 in the first embodiment. The other configurations and actions of the magnetic resonance imaging apparatus in the fourth embodiment do not differ from those of the magnetic resonance imaging apparatus 1 in the first embodiment substantially. Therefore, only a structure of the first positioning mechanism 6 is illustrated with attaching same signs to the same configurations, and explanations of the same configurations are omitted.

The first positioning mechanism 6 included in the magnetic resonance imaging apparatus in the fourth embodiment has at least one blind hole 30 whose cross section is circular and at least one stepped pin 31 whose cross section is circular. It is preferable to prepare two or more combinations consisting of the blind holes 30 and the stepped pins 31 in the direction normal to the longitudinal direction L of the bed 3 after the positioning.

The blind holes 30 are formed on the floor plate 8A. On the other hand, the stepped pins 31 are attached to the bed 3 side by an arbitrary method. For example, through holes are formed on the bed 3 and the stepped pins 31 are inserted into the through holes of the bed 3 so that the tips of the stepped pins 31 project from the bed 3.

Note that, it is practical to prepare the convex part 6B in the gantry 2 side and to prepare the concave part 6A in the bed 3 side, respectively, as shown in FIG. 1, from a viewpoint of supplying electric power to the driving mechanism 5B of the top plate 5A and the like. Further, a sufficient interspace is formed between the convex part 6B in the gantry 2 side and the concave part 6A in the bed 3 side.

The stepped pin 31 can have a structure that a circular truncated cone is inversely connected with one end of a cylindrical pin so that the outer diameter of the tip becomes thinner. In the illustrated example, the stepped pin 31 has a structure having two connected circular truncated cones whose inclinations are different.

The outer diameter of the taper part 31A of the stepped pin 31 is smaller than the inner diameter of the blind hole 30. Therefore, in a state where the stepped pin 31 has been shallowly inserted in the blind hole 30 as much as the taper part 31A of the stepped pin 31 touches the edge of the blind hole 30, the stepped pin 31 can be displaced slightly against the blind hole 30.

On the other hand, the outer diameter of the non-taper part 31B of the stepped pin 31 is made to have a size which fits the blind hole 30. Therefore, in a state where the stepped pin 31 has been inserted in the blind hole 30 deeply enough up to the non-taper part 31B, the stepped pin 31 fits the blind hole 30.

Therefore, when the stepped pin 31 is shallowly inserted in the blind hole 30, the bed 3 can be temporarily fixed in the gantry 2 side. In addition, the position of the bed 3 can be finely adjusted depending on the gap between the taper part 31A and the blind hole 30. For this reason, the pin 7A in the bed 3 side which composes the second positioning mechanism 7 can be fitted in the slotted hole 7B of the floor plate 8B, with adjusting the position of the bed 3. After that, the bed 3 can be locked in the gantry 2 side by strongly pushing the stepped pin 31, which composes the first positioning mechanism 6, into the blind hole 30.

That is, the first positioning mechanism 6 included in the magnetic resonance imaging apparatus in the fourth embodiment has the structure which can finely adjust the position of the bed 3. Consequently, according to the magnetic resonance imaging apparatus in the fourth embodiment, an effect similar to that of the magnetic resonance imaging apparatus in the third embodiment can be obtained.

Note that, the blind hole 30 which constitutes the first positioning mechanism 6 may be tapered. In that case, the tapered and stepped pin 31, in which an inclination is smaller than that of the blind hole 30, or a cylindrical usual pin can be used.

(Other Embodiments)

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

For example, the first positioning mechanism 6 in the third or fourth embodiment can be also combined with the first positioning mechanism 6 in the first or second embodiment. In addition, in each embodiment, the second positioning mechanism 7 can also be configured by elements other than the slotted hole 7B and the pin 7A. For example, the second positioning mechanism 7 may also be configured by a hole, whose cross section is circular, and a pin 7A.

What is claimed is:

1. A magnetic resonance imaging (MRI) apparatus comprising:
   a MRI gantry including a magnet, a gradient coil, and a radio frequency coil; and
   a movable patient bed having an elongated longitudinal dimension and under-mounted casters for rolling independent movement of the bed with respect to said gantry,
   said bed including
   (a) a first attachment mechanism having a first structure disposed at a first end of said bed and configured to be attachable to and detachable from said MRI gantry, and
   (b) a second attachment mechanism having a second structure, different from said first structure, disposed at a predetermined position longitudinally displaced from said first end of the bed and configured to be detachably affixed at a predetermined position relative to said gantry, said second attachment mechanism having a slotted hole and a pin that is inserted into the slotted hole when said bed is positioned relative to said gantry, wherein the inserted pin projects toward a plate on which the slotted hole is formed.

2. A magnetic resonance imaging apparatus according to claim 1, wherein said movable bed includes:
   a top plate configured to set a patient upon; and
   a driving mechanism configured to drive said top plate, said driving mechanism being controlled by electric power supplied from a control system through said gantry.

3. A magnetic resonance imaging apparatus according to claim 1,
   wherein said movable bed is configured to be positioned relative to said gantry in a horizontal direction at a first position corresponding to one of different positions of an end of said movable bed distant from said gantry after a positioning of the movable bed in the horizontal direction at a second position corresponding to another one of the different positions of an end of the movable bed near said gantry.

4. A magnetic resonance imaging apparatus according to claim 3,
   wherein said movable bed is configured to be locked by a positioning, in the horizontal direction, at the first position after a temporary joint by the positioning, in the horizontal direction, at the second position.

5. A magnetic resonance imaging apparatus according to claim 1, wherein:
said first attachment mechanism is configured for a positioning, in a horizontal direction, at a first position corresponding to one of different positions of said first end of said movable bed near said gantry, said first attachment mechanism having a structure to adjust a direction of said movable bed, in the horizontal direction, relative to said gantry; and
said second attachment mechanism is configured for a positioning, in the horizontal direction, at a second position corresponding to another one of the different positions of an opposite end of said movable bed distant from said gantry.

6. A magnetic resonance imaging apparatus of claim 1, wherein:
said first attachment mechanism is configured for a positioning, in a horizontal direction, at a first position corresponding to one of different positions of said first end of said movable bed near said gantry, said first attachment mechanism having a structure to adjust a position in a direction normal to the longitudinal direction of said movable bed; and
said second attachment mechanism is configured for a positioning, in the horizontal direction, at a second position corresponding to another one of the different positions of an end of the movable bed distant from said gantry.

7. A magnetic resonance imaging apparatus according to claim 1, wherein:
said first attachment mechanism is configured for a positioning, in a horizontal direction, at a first position corresponding to one of different positions of said first end of the movable bed near said gantry; and
said second attachment mechanism is configured for a positioning, in the horizontal direction, at a second position corresponding to another one of the different positions of an end of the movable bed distant from said gantry, said second attachment mechanism being configured to operate together with a positioning of said movable bed by said first attachment mechanism.

8. A magnetic resonance imaging apparatus according to claim 1, further comprising:
a plate disposed for movement of said bed there-over and configured to detachably fix said movable bed at one or more of the different positions, said plate being rigidly connected with said gantry.

9. A magnetic resonance imaging apparatus comprising:
a gantry including a magnet, a gradient coil, and a radio frequency coil; and
a movable bed configured to be positioned relative to said gantry by a positioning system having different structures for attaching said movable bed at respectively corresponding different positions in a longitudinal direction of said movable bed; and
a plate configured to fix said movable bed at one or more of the different positions so as to be detachable, said plate being rigidly connected with said gantry,
wherein at least one of said movable bed and said plate has a hole or a slot as at least one of the different structures while the other has a pin or a hook as at least one of the different structures for insertion into the hole or the slot when said movable bed is positioned relative to said gantry, and wherein the inserted pin or the inserted hook projects toward said plate.

10. A magnetic resonance imaging apparatus comprising:
a gantry including a magnet, a gradient coil, and a radio frequency coil; and
a movable bed configured to be positioned relative to said gantry by a positioning system having different structures for attaching said movable bed at respectively corresponding different positions in a longitudinal direction of said movable bed,
wherein said movable bed is configured to be positioned relative to said gantry by a slotted hole and a pin inserted into the slotted hole when said movable bed is positioned relative to said gantry, at a position corresponding to one of the different positions on a side of the movable bed distant from said gantry, the inserted pin projecting toward a plate on which the slotted hole is formed.

11. A method of positioning a movable bed having a longitudinal dimension and mounted on casters for rolling independent movement with respect to a magnetic resonance imaging (MM) apparatus, said method comprising:
moving the movable bed from a position separated and out of alignment with an MRI gantry to a predetermined position attached to a gantry of the magnetic resonance imaging apparatus using a first attachment mechanism having a first structure disposed at a first end of said bed; and
further moving the movable bed relative to the gantry to a second different position aligned in a longitudinal direction with the gantry using a second attachment mechanism having a second structure different from said first structure and located longitudinally distant from said first end of the bed, said second attachment mechanism having a slotted hole and a pin that is inserted into the slotted hole when said bed is positioned relative to said gantry, wherein the inserted pin projects toward a plate on which the slotted hole is formed.

12. A bed for a magnetic resonance imaging (MRI) apparatus comprising:
a movable patient bed main body having an elongated longitudinal dimension and under-mounted casters for rolling independent movement of the bed with respect to an MRI gantry, said bed including a top plate configured to set a patient upon;
a first attachment mechanism having a first structure disposed at a first end of said bed and configured for a positioning and temporary attachment of said bed main body to an MRI gantry at a first position; and
a second attachment mechanism having a second structure, different from said first structure, disposed at a predetermined position longitudinally displaced from said first end of the bed and configured for a positioning and temporary attachment of said bed main body at a second position different from the first position in a longitudinal direction of said bed main body, said second attachment mechanism having a slotted hole and a pin that is inserted into the slotted hole when said bed is positioned relative to said gantry, wherein the inserted pin projects toward a plate on which the slotted hole is formed.

13. A bed for the magnetic resonance imaging apparatus according to claim 12,
wherein said bed main body is configured to be positioned in a height direction of said top plate by contacting a caster, for moving said bed main body, with a floor.

14. A bed for the magnetic resonance imaging apparatus according to claim 13, wherein said first positioning mechanism and said second positioning mechanism are configured to enable the respective positionings in a state that the caster is contacting with the floor.

15. A bed for the magnetic resonance imaging apparatus according to claim 12,
wherein said bed main body is configured to be restricted to move in a horizontal direction by locking a drive of a caster for moving said bed main body.

* * * * *